United States Patent [19]

Esselborn et al.

[11] 4,086,100

[45] Apr. 25, 1978

[54] RUTILE-CONTAINING LUSTROUS PIGMENTS

[75] Inventors: Reiner Esselborn; Horst Bernhard, both of Darmstadt, Germany

[73] Assignee: Merck Patent Gesellschaft mit beschrankter Haftung, Darmstadt, Germany

[21] Appl. No.: 754,698

[22] Filed: Dec. 27, 1976

Related U.S. Application Data

[63] Continuation of Ser. No. 616,843, Sep. 25, 1975.

[30] Foreign Application Priority Data

May 22, 1975 Germany ............................ 2522572

[51] Int. Cl.$^2$ ............................ C09C 3/06; C09C 1/36
[52] U.S. Cl. .................................... 106/291; 106/300
[58] Field of Search ................................ 106/291, 300

[56] References Cited

U.S. PATENT DOCUMENTS

| | | | |
|---|---|---|---|
| 2,316,841 | 4/1943 | Cole | 106/300 |
| 3,087,828 | 4/1963 | Linton | 106/291 |
| 3,342,617 | 9/1967 | Jackson | 106/291 |
| 3,627,553 | 12/1971 | Clark et al. | 106/291 X |
| 3,634,119 | 1/1972 | Klenke | 106/291 |
| 3,650,790 | 3/1972 | Klenke et al. | 106/291 |
| 3,711,308 | 1/1973 | Brand et al. | 106/291 |

*Primary Examiner*—Patrick P. Garvin
*Assistant Examiner*—William G. Wright
*Attorney, Agent, or Firm*—Millen & White

[57] ABSTRACT

Mica flake-based lustrous pigments having a plurality of $TiO_2$ and $SnO_2$ layers thereon comprising at least one succession of rutile/$SnO_2$/rutile have improved properties, including light and weathering fastness.

16 Claims, No Drawings

RUTILE-CONTAINING LUSTROUS PIGMENTS

This is a continuation of application Ser. No. 616,843, filed Sept. 25, 1975.

BACKGROUND OF THE INVENTION

This invention relates to lustrous mica-flake pigments coated with $TiO_2$ and $SnO_2$.

A whole series of mica flake-based lustrous pigments coated with metal oxides has been known, e.g. from U.S. Pat. Nos. 3,087,828; 3,087,829; and 3,711,308; German patent specification No. 2,009,566 and German published specification No. 2,214,545. However, for special purposes, the light fastness and the weathering resistance of all of these pigments leaves something to be desired due primarily to the fact that in these pigments the $TiO_2$ is present in the anatase modification which is evidently favored by the mica substrate.

There are also known mica flake-based lustrous pigments which contain both $TiO_2$ and $SnO_2$. The tin oxide is either present as a surface coating on a $TiO_2$ coating or as a mixed precipitate with $TiO_2$. See, e.g., German patent specification No. 1,467,468. X-ray investigation of such pigments shows that the $TiO_2$, in spite of its tin content, is present in the anatase modification. According to published German specification No. 2,214,545, pigments are preferred in which the metal oxide layer consists preponderantly of rutile $TiO_2$ plus a small amount of tin oxide, with the concentration of the tin oxide being greater in the regions closest to the mica. The $SnO_2$ content of the metal oxide layer is preferably 0.5 to 5 wt. % but in no case to more than 20 wt. %. However, it has been found that these pigments contain $TiO_2$ which is not completely and not reproducibly in the rutile form but instead is very frequently present at least partially in the anatase form, although it is stated in published German patent specification No. 2,214,545 that the $TiO_2$ was present "substantially in rutile form."

Thus, it has been known for some time that, on the one hand, $SnO_2$ acts as catalyst for the conversion of anatase into rutile and that, on the other hand, mica favors the formation of the anatase modification of the $TiO_2$. Nevertheless, a satisfactory solution to the problem of producing rutile-containing pigments does not exist.

It is an object of this invention to provide lustrous pigments based on mica flakes coated with $TiO_2$ having improved properties in which the $TiO_2$ is present completely and reliably as rutile, even if the pigments have a comparatively thick layer of $TiO_2$ exhibiting interference colors. It is another object of this invention to provide such pigments which, compared to comparable pigments in which the anatase modification is present, display considerable technical advantages in use, including better light and weathering fastness. It is still another object to provide processes for the production and use of such pigments. Other objects will become apparent to those skilled in the art.

SUMMARY OF THE INVENTION

According to this invention, there are provided mica flake-based pigments with improved properties having a succession of metal oxide layers on the mica flakes, consisting essentially of $TiO_2$ and $SnO_2$, said pigments being characterized by the feature that the layers alternate and consist at least of the sequence rutile/$SnO_2$/rutile. In addition, said metal oxide layers, especially the $SnO_2$ layers, can optionally contain aluminium oxide.

DETAILED DISCUSSION

Such pigments have hitherto not been described. The arrangement of the metal oxide layers according to this invention is critical to the improved properties of the novel pigments. Surprisingly, the first layer, i.e., the $TiO_2$ layer directly in contact with the surface of the mica flakes must have a very small thickness, i.e., no more than about 25 nm., in order to provide satisfactory rutile pigments. In general, the layer thickness is from 0.1 to 25 nm. However, even thinner layers which are too thin to be measured with accuracy, are sufficient to provide pigments with satisfactory rutile layers. Admittedly, the $TiO_2$ layer directly in contact with the surface of the mica is still subject to the anatase-inducing influence of the mica, but evidently provides an acceptable and uniform covering of the mica surface which is a prerequisite for a uniform and acceptable $SnO_2$ coating. According to X-ray analysis, upon calcining, the $TiO_2$ layer is converted completely into rutile.

To the titanium hydroxide-coated mica flakes is then applied an intermediate layer of $SnO_2$, preferably of a thickness of about 2 to 25 nm. This $SnO_2$ layer, in an especially preferred embodiment, consists solely of $SnO_2$ or, optionally, like the $TiO_2$ layers, can contain certain amounts of $Al_2O_3$ or a hydrated form thereof, e.g., up to about 10%, preferably up to about 7%, of the total metal oxide content of the $SnO_2$ layer.

The total amount of $SnO_2$ in the rutile/$TiO_2$/rutile layers is preferably 5 wt. % or more, preferably about 8 to 30 wt. % of the total metal oxide content of the alternating rutile/$SnO_2$ layers. $SnO_2$ contents of up to 90 wt. % are technically possible but usually are uneconomical.

Over the $SnO_2$ layer is then provided a further layer of $TiO_2$, which in the final pigment, like the first $TiO_2$ layer is completely in the form of rutile. This, or a like rutile layer if further intermediate metal oxide layers are provided, is preferably the top or covering layer. The thickness of this layer depends solely upon the desired interference color of the pigment. As a rule, it varies from about 20 to 200 nm. However, this range is not limiting since only the color is affected by the thickness. Thus, in principle, any amount or layer thickness can be deposited which is conventional for $TiO_2$-coated mica pigments, many of which are commercially available.

According to this invention a plurality of tin oxide layers, alternating between $TiO_2$ layers, can be applied to the mica flakes so that a multiple sandwich structure results. In this case, the interference color of the pigment is determined by the total construction of the metal oxide layers. The amounts of oxide, i.e., the layer thicknesses, necessary therefor are determined by the refractive index of the oxides and can be calculated according to known rules. It is essential, however, that the bottom layer in contact with the mica flake be a thin $TiO_2$ layer. As the top or covering layer either a rutile or an $SnO_2$ layer can be employed but a rutile layer is preferred. As stated above, all or any of the individual oxide layers can have an $Al_2O_3$ content.

In a process aspect, this invention relates to a process for the production of such pigments which comprises coating uncoated mica flakes first with a thin layer of titanium hydroxide or a hydrate thereof; then depositing onto the thus-coated mica flakes a layer of tin hydroxide from a tin II salt solution in the presence of an oxidation agent; and then depositing another titanium hydroxide layer onto the coated mica flakes from a titanium salt solution. Optionally, any or all of these steps can be conducted in the presence of a soluble aluminum salt, thereby co-precipitating a hydrated form of aluminium oxide. Optionally also, the latter two coating steps can be repeated one or more times, in the same sequence. Thereafter, the mica flakes are washed, dried and calcined in the conventional manner.

The coating of the mica flakes can be accomplished according to conventional methods. The mica to be coated is normally slurried in deionized water and brought to an elevated temperature, e.g., about 40° to 90° C. The first thin $TiO_2$ layer is then deposited by precipitation of titanium hydroxide or a hydrate thereof from titanium salt solutions, e.g., from titanyl sulphate or titanium chloride. The reaction conditions are described in the literature, e.g., in German patent specification No. 2,009,566. This first $TiO_2$ layer should be as thin as possible in order to provide a pigment which contains roentgenographically pure rutile. The amount of titanium salt necessary for the selected mica surface can be calculated in the usual way. The coating operation is stopped when the desired layer thickness, up to a maximum of 25 nm., is reached.

Next, the tin hydroxide is deposited on the thus-coated mica. Contrary to the statements in the previously published literature, the coating of the mica flakes coated with $TiO_2$, with the formation of lustrous pigments, is accomplished best not with Sn IV salt solutions but instead with Sn II salt solutions in the presence of an oxidation agent. It is evidently important for this process that the oxidation occurs only slowly and during the precipitation. Under these conditions, one obtains, surprisingly, smooth tin dioxide hydrate layers with a previously unachievable uniformity.

It has been found, surprisingly, that for the achievement of satisfactory layers, the presence in the precipitating bath of a small amount of a soluble aluminium salt from which $Al_2O_3$ is subsequently formed, is desirable. Although the influence of the aluminium ions and/or of the aluminium oxide or its hydrate cannot be completely explained, three phenomena are especially worth mentioning. Surprisingly, the co-precipitation of aluminium hydroxide with the Ti or Sn hydroxide prevents crack formation which frequently appears when tin dioxide hydrate layers of high water content are calcined. Also, the addition of the aluminium salts appears to promote the formation of smooth tin dioxide layers and the quantitative deposition of the precipitates on the mica surface.

For the deposition of the tin oxide layer, the suspension containing mica flakes coated with a $TiO_2$ hydrate is adjusted by the addition of an acid, e.g., hydrochloric acid, to a pH value of 0.5 to 3.0, preferably about 1.0 to 2.5. The addition of the tin salt solution is then conducted in such a manner that the precipitate is deposited immediately and quantitatively as it forms. Thus, per unit time, there can be supplied to the mica slurry only such amount of the salt solutions to the reaction which the surface to be coated can take up per unit time. This is conveniently achieved by adding an aqueous solution of the tin salt slowly to the warmed suspension of the mica flakes. The acidity of the aqueous solution of the tin salt is adjusted in the usual manner, e.g., with hydrochloric acid, to a molarity of acid of between about 0.1 and 5.

As soluble tin salts, especially preferred are tin II chloride and tin II sulphate. However, the anion is not critical. The concentration of the tin II salt solution can be varied over a wide range but generally for reasons of expediency, is preferably from 0.1 to 3 moles per liter.

The tin salt solution optionally and preferably contains a water-soluble aluminium salt, e.g., aluminium chloride, acetate, nitrate and sulphate, as well as alkali metal aluminium mixed salts, e.g., potassium, sodium and ammonium aluminium sulphate. Preferably, about 0.01 to 2 moles Al per mole $Sn^{+2}$ is present, more preferably about 0.1 to 1 mole. It will be apparent that the aluminium salt can be added concurrently as a separate salt solution. If aluminium salts are added to the mica flake slurry, both metal ions should, in any case, be present simultaneously in the solution during the precipitation. Surprisingly, the desired effects are also achieved even in the presence of only trace amounts of Al ions. This is all the more surprising since only a very small part of the Al ions present in the case of the precipitation or formation of the hydrolysis products is incorporated into the pigment. Whereas the tin ions are deposited quantitatively on the mica flakes, a quite considerable part of the Al ions remains behind in the precipitation solution. This residual ionic Al can be found by back titration, e.g. in amounts of up to 96% of the Al salt used, from the aqueous phase after removal of the mica flakes. This applies similarly to the addition of aluminium ions to the titanium salt solutions. Methods for such additions are per se known. The $Al_2O_3$ content of the $TiO_2$ layers is not critical. However, not only the salt solution for the precipitation of the first thin $TiO_2$ layer but also those employed for the deposition of subsequent layers or any one thereof, preferably contain small amounts of water-soluble aluminium salts which co-precipitate to provide $Al_2O_3$ in the final metal oxide layer. If Al ions are present during the formation of the $SnO_2$ layer, the addition of more Al salts is not required to supply $Al_2O_3$ to subsequent oxide coatings because of residual Al ions present in the precipitation solution. These Al salts can be added to the titanium and tin salt solutions prior to the precipitation step or can be added separately and concurrently therewith to the mica flake slurry.

The deposition of the hydrated tin oxide is carried out in the presence of an oxidation agent, which can be present in the salt solution or added separately and concurrently therewith to the slurry. Oxidation agents which can be employed are those which oxidize Sn (II) ions into Sn (IV) ions, e.g., air, oxygen, $H_2O_2$ and hypochlorites. Especially useful are hydrogen peroxide and chlorates, especially potassium chlorate. The oxidation agent is expediently added in amounts about chemically equivalent to the tin salt solution employed. However, the concentrations and amounts are not critical and, if desired, atmospheric oxygen for the oxidation can be additionally introduced by the stirring of the slurry. Therefore, the oxidation agent can also be added in an excess or in a deficient amount. The optimum conditions in each case can easily be ascertained by routine experiments. Expediently, the aqueous solution of the oxidation agent is added separately from but simultaneously with the metal salt solution. It is normally preferable to avoid the introduction, by the oxidation agent, of further foreign ions, which may adversely influence the reaction.

It is expedient to maintain the pH value as constant as possible during the whole period of precipitation. This can be accomplished by the slow addition of, e.g., aqueous alkali metal hydroxide or ammonium hydroxide, preferably dilute aqueous sodium hydroxide solution or gaseous ammonia, as needed.

The production of the rutile pigments according to the invention and their quality depends in great part upon the special coating process by which the tin hydroxide is deposited. Hitherto, the coating with uniform $SnO_2$ layers and thus the dependable production of pure rutile pigments was not possible.

For pigments with only 3 metal oxide layers, the subsequent color-imparting $TiO_2$ layer is deposited in the desired layer thickness according to conventional methods, preferably after an interval of about 10 to 60 minutes after completion of the tin salt addition, in order to ensure complete hydrolysis of the tin salts. For details of the reaction conditions, see German patent specification No. 2,009,566, whose disclosure is incorporated by reference. The deposition takes place in the same way as the deposition of the first $TiO_2$ layer, e.g., employing titanium salt solutions at pH values of from 0.5 to 5.0 and at temperatures from about 50 to 100° C., the only difference being that the thickness of the layer can and preferably does exceed 25 nm. so as to produce a pigment with an interference color. Upon reaching the desired layer thickness, the coating operation is discontinued. During the coating, the color scale known from conventional lustrous pigments is passed through with increasing layer thickness, as illustrated below.

| Thickness of 2nd $TiO_2$ Layer in nm | Interference Color |
| --- | --- |
| about 40 | silver |
| about 55 | yellow |
| about 85 | red |
| about 95 | violet |
| about 130 | blue |
| about 150 | green |

With still thicker layers, colors of higher order appear. In the case of pigments with more than 3 layers, the Ti- and Sn-containing layers continue to be deposited alternatingly. In each case, reaction conditions which are known in the art can be employed.

All precipitations are so carried out that, in each case, temperature and pH value are kept as constant as possible during the whole coating operation. Furthermore, the addition of the reaction components is at a rate such that hydrated titanium or tin oxide is deposited immediately and quantitatively on the mica flakes as it is precipitated. Thus, per unit time, only such an amount of the reactants is supplied to the reaction which the surface of the mica to be coated can take up per unit time. Preferably, the various depositions are carried out successively, without isolation of the resulting intermediate coated products, although, in principle, a separation, washing and conceivably also calcination of the products is possible after each deposition. However, such isolations generally are omitted for economic reasons. The deposition of the various alternating layers is conducted in the same manner, with the final covering layer being either $TiO_2$ or $SnO_2$ but preferably the former.

The coated mica flakes are separated in the usual way from the slurry, are thoroughly washed with water and then dried. The coated mica flakes are then subjected to a conventional calcination process, e.g., for about 10 minutes up to about 4 hours at temperatures of up to about 1100° C., preferably from about 600° to 1000° C.

After this treatment, one obtains rutile pigments, the X-ray analysis of which no longer shows anatase lines.

The new pigments according to the invention can be produced from mica flakes conventionally employed for this purpose. The most frequently employed mica is muscovite. As a rule, the mica flakes have a diameter of about 5 to 200 microns and a thickness of about 0.1 to 5 microns, preferably about 0.5 micron.

Depending on the desired color shade, the new pigments contain metal oxide layers on the mica flakes in a total thickness of about 20 to about 200 nm., corresponding to a metal oxide content for the coated flakes of about 10 to about 90 wt. %. As a rule, pigments with a metal oxide content substantially lower than 5 wt. % do not possess the desired lustrous quality. An accurate determination of the aluminium oxide content of the metal oxide layer is for all practical purposes not possible since aluminium is also contained in the mica itself. The precise $Al_2O_3$ content in the metal oxide layer is not critical. Instead, it is the presence of Al ions during the precipitation of the hydrolysis products formed from the tin salts which appears essential to the improved results achieved. From the values obtained in the case of back titration, it can, however, be deduced that the proportion of $Al_2O_3$ in the $SnO_2$ layer of the final pigment varies from traces, e.g., 0.001 wt. %, to about 10%, with 7% ordinarily not being exceeded.

Typical examples of the pigments of this invention have the following composition:

| Mica Flake Pigments | Metal Oxide Coating |
| --- | --- |
| 25 to 90 wt. % mica | 0 to 10 wt. % $Al_2O_3$ |
| 7 to 70 wt. % $TiO_2$ (rutile) | 60 to 95 wt. % $TiO_2$ |
| 3 to 25 wt. % $SnO_2$ | 5 to 30 wt. % $SnO_2$ |

However, depending on the selected thickness of the respective metal oxide layers, pigments of this invention can also be obtained whose analyses vary considerably from the above values.

The pigments of this invention can be employed in the same manner as known mica flake pigments. They are especially suited for those fields of use where light fastness is of primary importance, e.g., motor car lacquers, and in cosmetics, where definite and very differentiated color nuances are desired. They are also well suited for the coloring of synthetic resins. The concentration thereof in the final compositions varies, depending upon the field of use, over a wide range, e.g., between 0.1 and 80%.

They can also be employed as starting materials for the production of other lustrous pigments. For example, the novel pigments can advantageously be coated in per se known manners with one or more further layers, e.g., with silicates, iron oxides, chromium oxides, $Al_2O_3$, zirconium dioxide, as well as dyestuffs and/or colored lakes, especially Al colored lakes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

60 g. of muscovite (diameter of 20 – 40μ) are suspended in 1.5 liters of completely deionized water. The pH of the suspension is brought to 2.2 with dilute hydrochloric acid. The suspension is then heated to 75° C. To the heated slurry is slowly added with stirring 30 ml. of a solution of 150 g. $TiCl_4$ and 50 g. HCl per liter (solution I), simultaneously with a 15% aqueous sodium hydroxide solution at a rate which maintains the pH constantly at 2.2. About 10 minutes after the addition is completed, 300 ml. of a tin chloride solution (19.1 g. $SnCl_2.2H_2O$ per liter of 5% hydrochloric acid, solution II) is slowly added to the slurry with stirring, simultaneously with 300 ml. of a potassium chlorate solution (4.3 g. $KClO_3$ per liter) and a 15% aqueous sodium hydroxide solution so as to keep the pH value constantly at 2.2.

About ½ hour after the addition is complete, about 270 ml. of solution I is again added while keeping the pH value constant. The pigment acquires a strong, silvery luster. The coating operation is discontinued and the suspension is further stirred for about 1 hour at 75° C. Then the pigment is filtered off, washed free of salts with completely deionized water, dried and calcined at 950° C. for half an hour. The pigment displays a strong, silvery luster. X-ray analysis shows that the $TiO_2$ is present in rutile form only. The pigment consists of 72.4% mica, 23.0% $TiO_2$ and 4.6% tin dioxide.

EXAMPLE 2

The following solutions are employed:
Solution I: A solution of titanium tetrachloride in hydrochloric acid (15% $TiCl_4$ and 4% HCl);
Solution II: A solution of 38.2 g. $SnCl_2.2H_2O$ in 1000 ml. 5% hydrochloric acid; and
Solution III: A solution of 8.3 g. $KClO_3$ in 1000 ml. water.

60 g. of muscovite (diameter 10 – 40μ) are suspended in 2 liters completely deionized water and the pH value of the suspension adjusted to 2.2 with Solution I. The suspension is heated to 70° C. While stirring, 30 ml. of Solution I are slowly added simultaneously with a 15% aqueous sodium hydroxide solution at a rate which maintains the pH value of the slurry at a constant 2.2. After about ¼ hour after completion of the addition of Solution I, during which time stirring is continued, Solution II and Solution III are slowly run in simultaneously at about the same rate, while maintaining the pH value constant at 2.2 with 15% aqueous sodium hydroxide solution. About ½ hour after completion of the addition, Solution I is again added in the same manner as the first coating operation. During this coating step, the mica flakes exhibit various interference colors, depending on the amount of Solution I added. Upon reaching the blue interference color (about 800 ml. of Solution I), the coating operation is stopped. The suspension is then stirred for about 1 hour. The pigment is filtered off, washed with water, dried and calcined for 30 minutes at 950° C. Roentgenographic investigation shows that the $TiO_2$ layer has only the rutile form. The pigment exhibits very good luster and luminescent color power. It contains 50.4% mica, 43.1% $TiO_2$ and 6.5% $SnO_2$.

EXAMPLE 3

60 g. of muscovite with a flake diameter of about 10 – 50 nm. are suspended in 1 liter completely deionized water. The suspension is adjusted to pH 2.2 with dilute hydrochloric acid. After heating to 75° C., titanium hydroxide is first deposited on the flakes employing 30 ml. of a solution of 150 g. of $TiCl_4$ in 1000 ml. of 5% hydrochloric acid in the manner described above, keeping the pH value at a constant 2.2 with 15% aqueous sodium hydroxide solution. Subsequently, a layer of tin hydroxide is so deposited on the mica flakes by adding 300 ml. amounts of 10% hydrochloric acid containing tin II chloride at a concentration shown in Table I simultaneously with a like volume of $KClO_3$ solution of equivalent concentration as shown in Table I at the same flow in rate, again maintaining the pH value at a constant 2.2 by the simultaneous addition of 15% aqueous sodium hydroxide solution. About 20 minutes after the addition is completed, the flakes are then coated with titanium hydroxide in the same manner as the first coating step employing 270 ml. of a solution of 150 g. $TiCl_4$ in 1000 ml. of 5% hydrochloric acid, again maintaining the pH value at a constant 2.2 by the simultaneous addition of 15% aqueous sodium hydroxide solution.

After conclusion of the coating operation, the coated mica flakes are filtered off, washed with completely deionized water, dried at 100° C. and subsequently calcined at 950° C. for 30 minutes. The pigments exhibit a strong silvery luster. In all cases, the $TiO_2$ is present solely in rutile form (roentgenographic detection). Table I is a summary of the coating conditions and the composition of the pigments thus-obtained.

TABLE I

| Experiment | Concentration of $SnCl_2$ Solution ($SnCl_2.2H_2O$ in g/l.) | Concentration of $KClO_3$ Solution in g/l. | Composition of the Oxide Layers | | |
|---|---|---|---|---|---|
| | | | Inner Layer (% $TiO_2$) | Middle Layer (% $SnO_2$) | Outer Layer (% $TiO_2$) |
| A | 19.1 | 4.3 | 8 | 17 | 75 |
| B | 28.6 | 6.0 | 8 | 23 | 69 |
| C | 38.2 | 8.6 | 7 | 29 | 64 |

EXAMPLE 4

Analogously to Example 3, muscovite is coated with 3 successive layers of titanium hydroxide, tin hydroxide and titanium hydroxide, in a series of experiments in which the pH is maintained at other constant values during the tin hydroxide precipitation. The coating conditions, insofar as they vary from those of Example 3, are summarized in Table II. In all cases, there is obtained a strongly glossy silver pigment, which contains $TiO_2$ solely in rutile form.

TABLE II

| | | Coating with Tin Hydroxide | | | | | |
|---|---|---|---|---|---|---|---|
| | | Concentration of SnCl$_2$ Solution (SnCl$_2$.2H$_2$O, g/l.) | Amount of SnCl$_2$ Solution (ml.) | Concentration of HClO$_3$ Solution (g/l.) | Composition of the Oxide Layers | | |
| Experiment | pH | | | | Inner Layer (% TiO$_2$) | Middle Layer (% SnO$_2$) | Outer Layer (% TiO$_2$) |
| D | 2.2 | 19.1 | 300 | 4.3 | 8 | 17 | 75 |
| E | 1.8 | 19.1 | 300 | 4.3 | 8 | 17 | 75 |
| F | 1.5 | 19.1 | 300 | 4.3 | 8 | 17 | 75 |
| G | 1.0 | 19.1 | 300 | 4.3 | 8 | 17 | 75 |

EXAMPLE 5

Analogously to Example 3, in a series of experiments pigments are prepared in which the two TiO$_2$ layers vary in layer thickness. The same solutions are employed as in Example 3 but the volume of the solutions used for the two coating steps is varied. Also, the tin hydroxide coating step is conducted at a pH value of 1.5. In all cases, silver pigments are obtained with very good gloss and which contain the TiO$_2$ solely in rutile form.

Table III is a summary of the experimental conditions employed and the composition of the pigments obtained.

TABLE III

| | 1st Coating with Titanium Hydroxide | | Coating with Tin Hydroxide | 2nd Coating with Titanium Hydroxide | | Composition of the Oxide Layers | | |
|---|---|---|---|---|---|---|---|---|
| Experiment | pH | Amount of TiCl$_4$ Solution, ml. | pH | pH | Amount of TiCl$_4$ Solution, ml. | Inner Layer (% TiO$_2$) | Middle Layer (% SnO$_2$) | Outer Layer (% TiO$_2$) |
| H | 2.2 | 60 | 1.5 | 2.2 | 240 | 17 | 17 | 66 |
| I | 2.2 | 30 | 1.5 | 2.2 | 270 | 8 | 17 | 75 |
| K | 2.2 | 15 | 1.5 | 2.2 | 285 | 4 | 17 | 79 |

EXAMPLE 6

Analogously to Experiment A described in Example 3, muscovite is coated with 3 successive layers of titanium hydroxide, tin hydroxide and titanium hydroxide, except that instead of the KClO$_3$ solution, there is used as oxidation agent a chemically equivalent amount of 5% hydrogen peroxide. The pigment obtained exhibits an excellent luster, a silvery color and contains the TiO$_2$ solely in rutile form. The analysis data agree completely with those of the product according to Experiment A.

EXAMPLE 7

5.0 kg. of muscovite with a particle diameter of about 10 to 40 μ are suspended in 100 liters of completely deionized water. The pH is adjusted to 2.1 with dilute hydrochloric acid. The suspension is heated to 75° C. and with stirring there is added 2.5 liters of an aqueous solution of 150 g TiCl$_4$ and 40 g. HCl per liter, over a period of 20 minutes, simultaneous with a 30% aqueous sodium hydroxide solution at a rate which maintains the pH value at a constant 2.1. Subsequently, a solution of 162 g. KClO$_3$ in 2.5 liters of water is added and a solution of 717 g. SnCl$_2$.2H$_2$O in 2.86 liters concentrated hydrochloric acid in 21.8 liters water is passed in at a rate of about 10 liters/hour, concurrently with 30% aqueous sodium hyroxide solution at a rate which keeps the pH value at a constant 2.1. The slurry is allowed to stand for about 30 minutes and the final titanium hydroxide coating is applied, employing a solution of 150 g. TiCl$_4$ and 50 g. HCl per liter, again keeping the pH value at 2.1 with 30% aqueous sodium hydroxide solution. During the coating, the pigment acquires a strong silver gloss, whereupon the coating operation is stopped. The slurry is filtered as usual, the mica flakes washed and dried and subsequently calcined at 960° C. for 35 minutes. Roentgenographic investigation reveals that the TiO$_2$ is present solely in the rutile form. The product contains 68% mica, 26% TiO$_2$ and 6% SnO$_2$.

EXAMPLE 8

The following solutions are employed:

Solution I: A hydrochloric acid-TiCl$_4$ solution containing 10% TiCl$_4$, 5% HCl and 10 g. AlCl$_3$.6H$_2$O per liter;
Solution II: A hydrochloric acid-tin (II) solution containing 200 g. SnCl$_2$.2H$_2$O, 50 g. HCl and 50 g. AlCl$_3$.6H$_2$O per liter; and
Solution III: A KClO$_3$ solution containing 40 g. KClO$_3$ per liter.

60 g. of muscovite with a diameter of about 10 to 40 μ are suspended in completely deionized water and the suspension is adjusted with Solution I to a pH value of 2.0. After heating to 75° C., 40 ml. of Solution I are slowly added simultaneously with a 15% aqueous sodium hydroxide solution so as to keep the pH value at a constant 2.0. About 15 minutes after addition is complete, 60 ml. of Solution II is added slowly simultaneously with 60 ml. of Solution III and with 15% aqueous sodium hydroxide solution at a rate which keeps the pH value at a constant 2.0. About 30 minutes after the addition of the tin solution is complete, in order to permit the hydrolysis to go to completion, the coating operation is continued in the same manner according to the following scheme, alternately employing titanium tetrachloride and tin chloride solutions, at a constant pH 2:

| Oxide Layer Produced | Solution I | Solution II | Solution III |
| --- | --- | --- | --- |
| TiO$_2$ | 320 ml. | — | — |
| SnO$_2$ | — | 60 ml. | 60 ml. |
| TiO$_2$ | 320 ml. | — | — |
| SnO$_2$ | — | 60 ml. | 60 ml. |
| TiO$_2$ | 320 ml. | — | — |
| SnO$_2$ | — | 60 ml. | 60 ml. |
| TiO$_2$ | 320 ml. | — | — |
| SnO$_2$ | — | 60 ml. | 60 ml. |

The product is worked up as in Example 1 and calcined at 900° C. for 40 minutes. The pigment exhibits a strong green interference color with good gloss. Roentgenographic investigation reveals the TiO$_2$ is solely in rutile form.

The pigment contains 40% mica, 35% rutile, 21% SnO$_2$ and about 3% Al$_2$O$_3$ (determined by back titration).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a lustrous mica flake pigment wherein the mica flakes are coated with a plurality of metal oxide layers consisting essentially of alternating layers of TiO$_2$ and SnO$_2$ in which each rutile layer is roentogenographically free from the anatase form, the improvement wherein the metal oxide layers comprise the sequence rutile/SnO$_2$/rutile and the innermost layer is rutile and wherein the thickness of the innermost rutile layer is a maximum of about 25 nm.

2. A pigment according to claim 1 wherein the outermost metal oxide layer is rutile.

3. A pigment according to claim 1 wherein the collective SnO$_2$ content of the metal oxide layers is 13.1 to 37.5 wt. %.

4. A pigment according to claim 1 wherein at least one of the rutile/SnO$_2$/rutile layers contains Al$_2$O$_3$ in a collective amount sufficient to prevent crack formation when tin dioxide hydrate layers of high water content are calcined and to promote the formation of smooth tin dioxide layers and the quantitative deposition of the precipitates on the mica surface.

5. A pigment according to claim 4 wherein each layer contains aluminium oxide, in an amount collectively of up to 10 wt. %.

6. A pigment according to claim 1 wherein the SnO$_2$ content of the pigment is about 3 to 25 wt. %.

7. A pigment according to claim 1 wherein the rutile content of the pigment is about 7 to 70 wt. %.

8. A mica flake pigment according to claim 1 wherein the metal oxide coating consists of three layers wherein the innermost layer consists of rutile, the middle layer consists of SnO$_2$ and the outermost metal oxide layer consists of rutile, wherein the SnO$_2$ content of the pigment is about 3 to 25 wt. % and of the metal oxides is about 13.1 to 37.5 wt. % and the rutile content of the pigment is about 7 to 70 wt. % and of the metal oxides is about 86.9 to about 62.5 wt. %.

9. A mica flake pigment according to claim 1 wherein the collective SnO$_2$ content of the metal oxide layers is at least 5 wt. %, wherein the SnO$_2$ layer contains aluminum oxide in an amount of up to 10 wt. % and wherein the outermost metal oxide layer is rutile of a thickness of at least 20 nm.

10. In a process for the production of a TiO$_2$ coated mica flake pigment comprising a layer on the mica flakes of TiO$_2$ in the rutile form only over a layer of SnO$_2$, wherein tin hydroxide and titanium hydroxide are precipitated successively onto the mica flakes from a tin salt solution and a titanium salt solution, respectively, and the thus-coated flakes are then washed, dried and calcined, the improvement which comprises coating the mica flakes first with a thin layer of titanium hydroxide of up to 25 nm. thickness; precipitating the layer of tin hydroxide onto the thus-coated mica flakes from a tin II salt solution; in the presence of an oxidizing agent and then depositing a further layer of titanium hydroxide onto the coated mica flakes.

11. A process according to claim 10 wherein the tin hydroxide is precipitated in the presence of KClO$_3$ as the oxidation agent.

12. A process according to claim 10 wherein at least tin hydroxide layer is formed in the presence of a water-soluble aluminium salt.

13. A process according to claim 10 wherein the titanium and tin hydroxide layers are formed successively without isolation of the intermediate products.

14. A process according to claim 10 wherein the final metal oxide layer deposited on the mica flakes is titanium hydroxide.

15. A process according to claim 10 wherein at least the tin hydroxide layer is formed in the presence of a water-soluble aluminum salt, and wherein the titanium and tin hydroxide layers are formed successively without isolation of the intermediate products.

16. A process according to claim 15 wherein the tin hydroxide is precipitated in the presence of KClO$_3$ as the oxidation agent.

* * * * *